US012558017B2

(12) United States Patent
Le et al.

(10) Patent No.: US 12,558,017 B2
(45) Date of Patent: *Feb. 24, 2026

(54) METHODS FOR MODELING NEUROLOGICAL DEVELOPMENT AND DIAGNOSING A NEUROLOGICAL IMPAIRMENT OF A PATIENT

(71) Applicant: Emotiv Inc., San Francisco, CA (US)

(72) Inventors: Tan Le, San Francisco, CA (US); Geoffrey Ross Mackellar, Sydney (AU)

(73) Assignee: Emotiv Inc., San Francisco, CA (US)

( * ) Notice: Subject to any disclaimer, the term of this patent is extended or adjusted under 35 U.S.C. 154(b) by 0 days.

This patent is subject to a terminal disclaimer.

(21) Appl. No.: 18/739,741

(22) Filed: Jun. 11, 2024

(65) Prior Publication Data

US 2024/0324940 A1 Oct. 3, 2024

Related U.S. Application Data

(60) Division of application No. 18/082,474, filed on Dec. 15, 2022, now Pat. No. 12,036,030, which is a
(Continued)

(51) Int. Cl.
*A61B 5/372* (2021.01)
*A61B 5/316* (2021.01)
(Continued)

(52) U.S. Cl.
CPC .............. *A61B 5/369* (2021.01); *A61B 5/316* (2021.01); *G16H 50/50* (2018.01)

(58) Field of Classification Search
None
See application file for complete search history.

(56) References Cited

U.S. PATENT DOCUMENTS

| | | | |
|---|---|---|---|
| 4,421,122 A | 12/1983 | Duffy | |
| 5,287,859 A | 2/1994 | John | |

(Continued)

FOREIGN PATENT DOCUMENTS

| | | |
|---|---|---|
| JP | 2014215963 A | 11/2014 |
| WO | 2004047636 A1 | 6/2004 |

(Continued)

OTHER PUBLICATIONS

Davis, Gene , et al., "Soft, Embeddable, Dry EEG Sensors for Real World Applications", 12th European Conference on Computer Vision, ECCV 2012; [Lecture notes in Computer Science], pp. 269-278, XP047544849.

(Continued)

*Primary Examiner* — Etsub D Berhanu
(74) *Attorney, Agent, or Firm* — Jeffrey Schox; Annabel Imbrie-Moore

(57) ABSTRACT

One variation of a method for modeling neurological development includes: aggregating electroencephalography (EEG) data that comprise multiple EEG signals of each user in a set of users, EEG signals of each user recorded on multiple distinct dates, the set of users comprising a plurality of users of various known neurological statuses; identifying a synchronization pattern trend within the EEG data of the set of users; and correlating the synchronization pattern trend with neurological development within the set of users.

9 Claims, 7 Drawing Sheets

S200

Block S210:
Aggregating a plurality of EEG signals of the patient, each EEG signal recorded on a distinct date Block S220:
Identifying a synchronization pattern trend in the EEG signals of the patient Block S230:
Comparing the synchronization pattern trend of the patient with a neurological impairment model correlated with a neurological impairment Block S230:
Diagnosing the patient with the neurological impairment based upon the comparison

Related U.S. Application Data continuation of application No. 16/456,449, filed on Jun. 28, 2019, now Pat. No. 11,553,870, which is a continuation of application No. 13/565,740, filed on Aug. 2, 2012, now abandoned.

(60) Provisional application No. 61/514,418, filed on Aug. 2, 2011.

(51) Int. Cl.
| | |
|---|---|
| *A61B 5/369* | (2021.01) |
| *G16H 50/50* | (2018.01) |

(56) References Cited

U.S. PATENT DOCUMENTS

| | | | |
|---|---|---|---|
| 6,201,982 | B1 | 3/2001 | Menkes et al. |
| 6,230,049 | B1 | 5/2001 | Fischell et al. |
| 6,801,803 | B2 | 10/2004 | Viertioe-Oja |
| 6,954,700 | B2 | 10/2005 | Higashida et al. |
| 7,639,145 | B2 | 12/2009 | Lawson et al. |
| 7,764,311 | B2 | 7/2010 | Bill |
| 7,844,324 | B2 | 11/2010 | Saerkelae et al. |
| 7,904,144 | B2 | 3/2011 | Causevic et al. |
| 7,933,644 | B2 | 4/2011 | Wong et al. |
| 7,962,204 | B2 | 6/2011 | Suffin et al. |
| 7,986,991 | B2 | 7/2011 | Prichep |
| 8,103,333 | B2 | 1/2012 | Tran |
| 8,108,036 | B2 | 1/2012 | Tran |
| 8,114,021 | B2 | 2/2012 | Robertson et al. |
| 8,137,270 | B2 | 3/2012 | Keenan et al. |
| 8,147,419 | B2 | 4/2012 | Krauss et al. |
| 8,190,248 | B2 | 5/2012 | Besio et al. |
| 8,190,249 | B1 | 5/2012 | Gharieb et al. |
| 8,271,075 | B2 | 9/2012 | Chuang et al. |
| 8,306,610 | B2 | 11/2012 | Mirow |
| 8,583,223 | B2 | 11/2013 | Maddess et al. |
| 8,652,040 | B2 | 2/2014 | Leboeuf et al. |
| 8,688,209 | B2 | 4/2014 | Verbitskiy |
| 8,690,769 | B2 | 4/2014 | Edman et al. |
| 8,725,243 | B2 | 5/2014 | Dilorenzo et al. |
| 8,838,215 | B2 | 9/2014 | John et al. |
| 9,179,854 | B2 | 11/2015 | Doidge et al. |
| 9,521,960 | B2 | 12/2016 | Lee et al. |
| 9,763,592 | B2 | 9/2017 | Le et al. |
| 9,867,548 | B2 | 1/2018 | Le et al. |
| 10,028,703 | B2 | 7/2018 | Le et al. |
| 10,108,264 | B2 | 10/2018 | Le et al. |
| 10,291,977 | B2 | 5/2019 | Mackellar et al. |
| 2001/0049480 | A1 | 12/2001 | John et al. |
| 2002/0029005 | A1 | 3/2002 | Levendowski et al. |
| 2002/0077560 | A1 | 6/2002 | Kramer et al. |
| 2003/0055355 | A1 | 3/2003 | Viertiö-Oja |
| 2003/0181795 | A1 | 9/2003 | Suzuki et al. |
| 2004/0012410 | A1 | 1/2004 | Liu et al. |
| 2004/0078219 | A1 | 4/2004 | Kaylor et al. |
| 2004/0122703 | A1 | 6/2004 | Walker et al. |
| 2004/0137639 | A1 | 7/2004 | Miyazaki et al. |
| 2004/0152957 | A1 | 8/2004 | Stivoric et al. |
| 2004/0236240 | A1 | 11/2004 | Kraus et al. |
| 2004/0249249 | A1 | 12/2004 | Lawson et al. |
| 2005/0079474 | A1 | 4/2005 | Lowe |
| 2005/0107723 | A1 | 5/2005 | Wehman et al. |
| 2005/0234329 | A1 | 10/2005 | Kraus et al. |
| 2005/0240087 | A1 | 10/2005 | Keenan et al. |
| 2005/0277826 | A1 | 12/2005 | Dunseath |
| 2005/0283053 | A1 | 12/2005 | Decharms |
| 2005/0288954 | A1 | 12/2005 | Mccarthy et al. |
| 2006/0009697 | A1 | 1/2006 | Banet et al. |
| 2006/0015034 | A1 | 1/2006 | Martinerie et al. |
| 2006/0063980 | A1 | 3/2006 | Hwang et al. |
| 2006/0143647 | A1 | 6/2006 | Bill |
| 2006/0167350 | A1* | 7/2006 | Monfre .............. A61B 5/1455 |
| | | | 128/920 |
| 2006/0173510 | A1 | 8/2006 | Besio et al. |

| | | | |
|---|---|---|---|
| 2006/0293921 | A1 | 12/2006 | Mccarthy et al. |
| 2007/0032737 | A1 | 2/2007 | Causevic et al. |
| 2007/0033634 | A1 | 2/2007 | Leurs et al. |
| 2007/0060831 | A1 | 3/2007 | Le et al. |
| 2007/0061735 | A1 | 3/2007 | Hoffberg et al. |
| 2007/0100246 | A1 | 5/2007 | Hyde |
| 2007/0113725 | A1 | 5/2007 | Oliver et al. |
| 2007/0150025 | A1 | 6/2007 | Dilorenzo et al. |
| 2007/0173733 | A1 | 7/2007 | Le et al. |
| 2007/0191727 | A1 | 8/2007 | Fadem |
| 2007/0208263 | A1 | 9/2007 | John et al. |
| 2007/0219455 | A1 | 9/2007 | Wong et al. |
| 2007/0225585 | A1 | 9/2007 | Washbon et al. |
| 2007/0238934 | A1 | 10/2007 | Viswanathan |
| 2007/0287931 | A1 | 12/2007 | Dilorenzo |
| 2007/0293731 | A1* | 12/2007 | Downs .................. G16H 40/67 |
| | | | 600/300 |
| 2008/0027345 | A1 | 1/2008 | Kumada et al. |
| 2008/0103368 | A1 | 5/2008 | Craine et al. |
| 2008/0108908 | A1 | 5/2008 | Maddess et al. |
| 2008/0146890 | A1 | 6/2008 | Leboeuf et al. |
| 2008/0177197 | A1 | 7/2008 | Lee et al. |
| 2008/0194981 | A1 | 8/2008 | Sarkela et al. |
| 2008/0242946 | A1 | 10/2008 | Krachman |
| 2008/0292194 | A1* | 11/2008 | Schmidt .............. G06T 7/0012 |
| | | | 382/131 |
| 2008/0294062 | A1 | 11/2008 | Rapoport et al. |
| 2008/0306895 | A1 | 12/2008 | Karty |
| 2009/0018405 | A1 | 1/2009 | Katsumura et al. |
| 2009/0024050 | A1 | 1/2009 | Jung et al. |
| 2009/0062676 | A1 | 3/2009 | Kruglikov et al. |
| 2009/0079607 | A1 | 3/2009 | Denison et al. |
| 2009/0083129 | A1 | 3/2009 | Pradeep et al. |
| 2009/0105576 | A1 | 4/2009 | Do et al. |
| 2009/0131764 | A1 | 5/2009 | Lee et al. |
| 2009/0137923 | A1 | 5/2009 | Suffin et al. |
| 2009/0163781 | A1 | 6/2009 | Say et al. |
| 2009/0163784 | A1 | 6/2009 | Sarpeshkar et al. |
| 2009/0214060 | A1 | 8/2009 | Chuang et al. |
| 2009/0227876 | A1 | 9/2009 | Tran |
| 2009/0247894 | A1 | 10/2009 | Causevic |
| 2009/0259137 | A1 | 10/2009 | Delic et al. |
| 2009/0292180 | A1 | 11/2009 | Mirow |
| 2009/0318779 | A1 | 12/2009 | Tran |
| 2009/0318825 | A1 | 12/2009 | Kilborn |
| 2009/0327068 | A1 | 12/2009 | Pradeep et al. |
| 2010/0004977 | A1 | 1/2010 | Marci et al. |
| 2010/0010336 | A1 | 1/2010 | Pettegrew et al. |
| 2010/0010364 | A1 | 1/2010 | Verbitskiy |
| 2010/0022820 | A1 | 1/2010 | Leuthardt et al. |
| 2010/0022907 | A1 | 1/2010 | Perez-Velazquez et al. |
| 2010/0042011 | A1 | 2/2010 | Doidge et al. |
| 2010/0049004 | A1 | 2/2010 | Edman et al. |
| 2010/0069735 | A1 | 3/2010 | Berkner |
| 2010/0094155 | A1 | 4/2010 | Prichep |
| 2010/0121572 | A1 | 5/2010 | Berardi et al. |
| 2010/0147913 | A1 | 6/2010 | Corets |
| 2010/0169409 | A1 | 7/2010 | Fallon et al. |
| 2010/0172522 | A1 | 7/2010 | Mooring et al. |
| 2010/0217100 | A1 | 8/2010 | Leboeuf et al. |
| 2010/0286549 | A1 | 11/2010 | John et al. |
| 2010/0312188 | A1 | 12/2010 | Robertson et al. |
| 2011/0038515 | A1* | 2/2011 | Jacquin .................. A61B 5/369 |
| | | | 382/160 |
| 2011/0046502 | A1 | 2/2011 | Pradeep et al. |
| 2011/0071364 | A1 | 3/2011 | Kuo et al. |
| 2011/0087125 | A1 | 4/2011 | Causevic |
| 2011/0098112 | A1 | 4/2011 | Leboeuf et al. |
| 2011/0172553 | A1 | 7/2011 | John |
| 2011/0184247 | A1 | 7/2011 | Contant et al. |
| 2011/0196211 | A1 | 8/2011 | Al-Ali et al. |
| 2011/0201904 | A1 | 8/2011 | Cusimano et al. |
| 2011/0245633 | A1 | 10/2011 | Goldberg et al. |
| 2011/0257502 | A1 | 10/2011 | Lee |
| 2011/0270117 | A1 | 11/2011 | Warwick et al. |
| 2011/0282232 | A1 | 11/2011 | Pradeep et al. |
| 2012/0101396 | A1 | 4/2012 | Solosko et al. |
| 2012/0108999 | A1 | 5/2012 | Leininger et al. |
| 2012/0156933 | A1 | 6/2012 | Kreger et al. |

(56) References Cited

U.S. PATENT DOCUMENTS

| | | |
|---|---|---|
| 2012/0197153 A1 | 8/2012 | Kraus et al. |
| 2012/0265088 A1 | 10/2012 | Snell |
| 2012/0330114 A1 | 12/2012 | Cheung et al. |
| 2013/0035579 A1 | 2/2013 | Le et al. |
| 2013/0178731 A1 | 7/2013 | Bosl |
| 2013/0317384 A1 | 11/2013 | Le |
| 2014/0038147 A1 | 2/2014 | Morrow |
| 2014/0171775 A1 | 6/2014 | Kilsgaard et al. |
| 2014/0223462 A1 | 8/2014 | Aimone et al. |
| 2014/0257073 A1 | 9/2014 | Machon et al. |
| 2014/0316230 A1 | 10/2014 | Denison et al. |
| 2014/0336473 A1 | 11/2014 | Greco |
| 2015/0150753 A1 | 6/2015 | Racette |
| 2015/0216437 A1 | 8/2015 | Mihajlovic |
| 2015/0216439 A1 | 8/2015 | Muraskin et al. |
| 2015/0297109 A1 | 10/2015 | Garten et al. |
| 2015/0351655 A1 | 12/2015 | Coleman |
| 2016/0029958 A1 | 2/2016 | Le et al. |
| 2016/0095535 A1 | 4/2016 | Hettrick et al. |
| 2016/0286287 A1 | 9/2016 | Slack |
| 2017/0027466 A1 | 2/2017 | Kerth et al. |
| 2017/0041264 A1 | 2/2017 | Khomami Abadi et al. |
| 2017/0319132 A1 | 11/2017 | Longinotti-Buitoni et al. |
| 2019/0113973 A1 | 4/2019 | Coleman et al. |
| 2019/0246982 A1 | 8/2019 | Mackellar et al. |
| 2019/0320979 A1 | 10/2019 | Le et al. |
| 2023/0225659 A1 | 7/2023 | Azemi et al. |

FOREIGN PATENT DOCUMENTS

| | | | |
|---|---|---|---|
| WO | 2009087486 A2 | 7/2009 | |
| WO | 2010147913 A1 | 12/2010 | |
| WO | WO-2012021789 A1 * | 2/2012 | ............. A61B 5/245 |
| WO | 2014150684 A1 | 9/2014 | |
| WO | 2016070188 A1 | 5/2016 | |

OTHER PUBLICATIONS

Park, Jeong-Hyeon , et al., "Multiscale Entropy Analysis of EEG from Patients Under Different Pathological Conditions", Fractais 15, 399 (2007). Fractals vol. 15, No. 4 (2007) 399-404.

Srinivasan, Jayarman , et al., "Heart Rate Calculation from Ensemble Brain Wave Using Wavelet and Teager-Kaiser Energy Operator", IEEE (2015).

Stam, Cornelius J., et al., "Nonlinear Synchronization in EEG and Whole-Head MEG Recordings of Healthy Subjects", Hum Brain Mapp. Jun. 2003; 19(2): 63-78, published Mar. 12, 2003.

Warchall, Julian , "A Multi-Channel EEG System Featuring Single-Wire Data Aggregation via FM-FDM Techniques", IEEE International Symposium on Circuits and Systems (ISCAS), May 22-25, 2016. (Year: 2016).

\* cited by examiner

S100

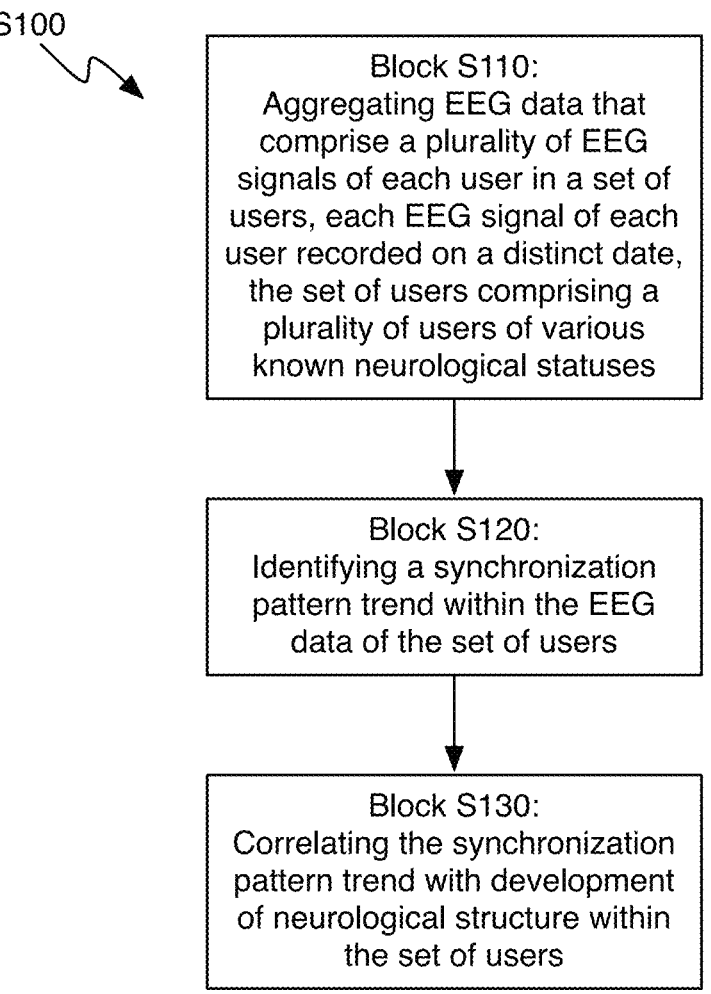

Block S110:
Aggregating EEG data that comprise a plurality of EEG signals of each user in a set of users, each EEG signal of each user recorded on a distinct date, the set of users comprising a plurality of users of various known neurological statuses Block S120:
Identifying a synchronization pattern trend within the EEG data of the set of users Block S130:
Correlating the synchronization pattern trend with development of neurological structure within the set of users

FIG. 1

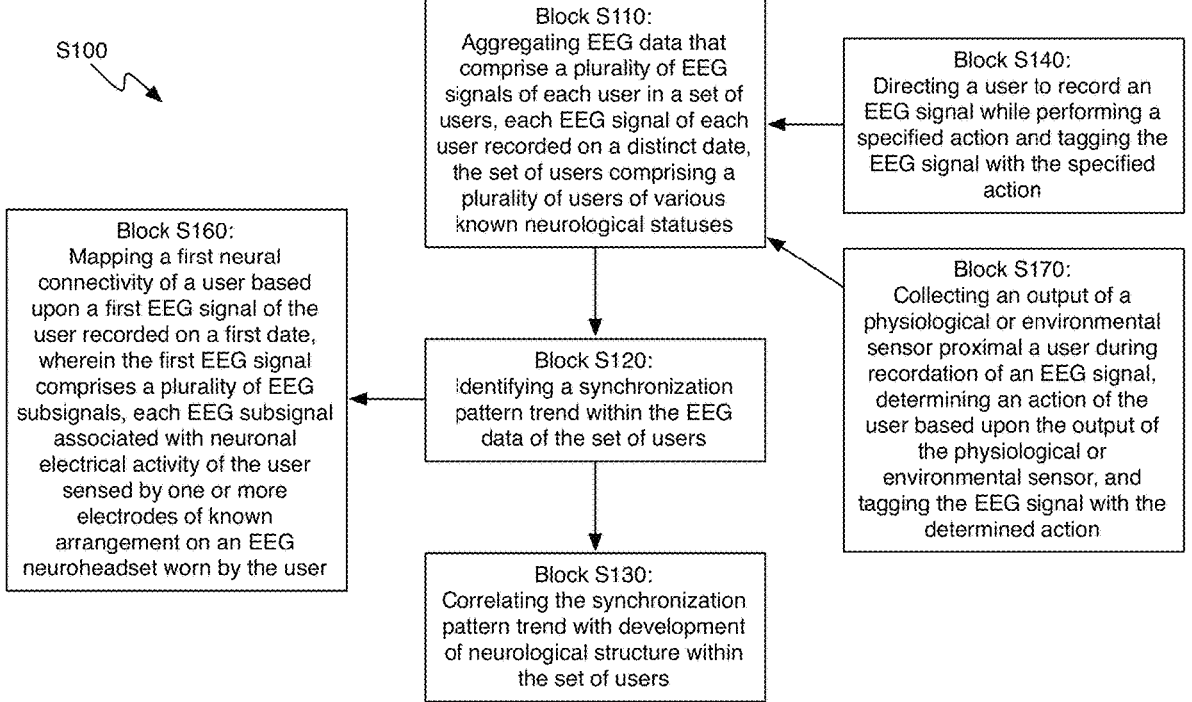

S100

Block S110:
Aggregating EEG data that comprise a plurality of EEG signals of each user in a set of users, each EEG signal of each user recorded on a distinct date, the set of users comprising a plurality of users of various known neurological statuses Block S140:
Directing a user to record an EEG signal while performing a specified action and tagging the EEG signal with the specified action Block S160:
Mapping a first neural connectivity of a user based upon a first EEG signal of the user recorded on a first date, wherein the first EEG signal comprises a plurality of EEG subsignals, each EEG subsignal associated with neuronal electrical activity of the user sensed by one or more electrodes of known arrangement on an EEG neuroheadset worn by the user Block S120:
Identifying a synchronization pattern trend within the EEG data of the set of users Block S170:
Collecting an output of a physiological or environmental sensor proximal a user during recordation of an EEG signal, determining an action of the user based upon the output of the physiological or environmental sensor, and tagging the EEG signal with the determined action Block S130:
Correlating the synchronization pattern trend with development of neurological structure within the set of users

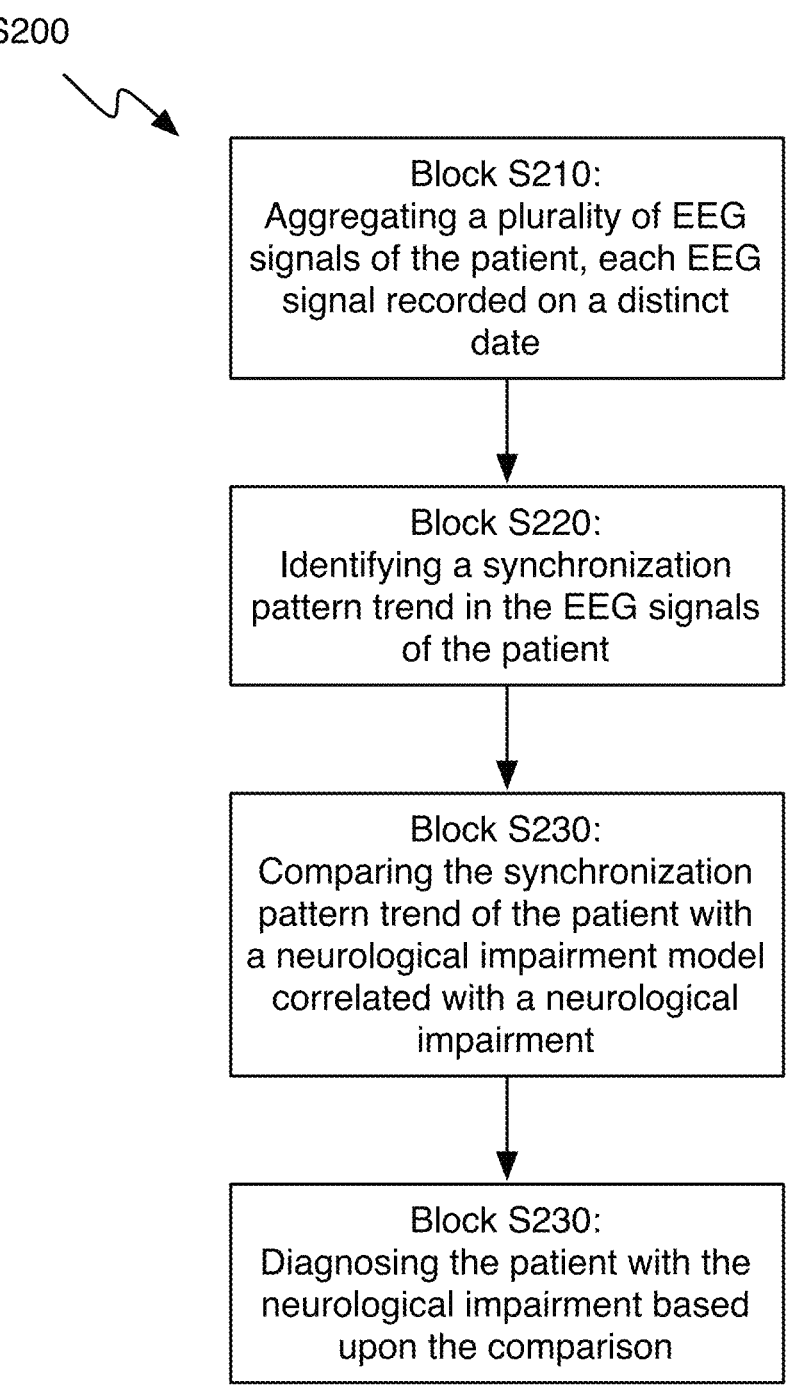

Block S210:
Aggregating a plurality of EEG signals of the patient, each EEG signal recorded on a distinct date Block S220:
Identifying a synchronization pattern trend in the EEG signals of the patient Block S230:
Comparing the synchronization pattern trend of the patient with a neurological impairment model correlated with a neurological impairment Block S230:
Diagnosing the patient with the neurological impairment based upon the comparison

METHODS FOR MODELING NEUROLOGICAL DEVELOPMENT AND DIAGNOSING A NEUROLOGICAL IMPAIRMENT OF A PATIENT

CROSS-REFERENCE TO RELATED APPLICATIONS

This application is a divisional of U.S. application Ser. No. 18/082,474, filed 15 Dec. 2022, which is a continuation of U.S. application Ser. No. 16/456,449, filed 28 Jun. 2019, which is a continuation of U.S. application Ser. No. 13/565, 740, filed 2 Aug. 2012, which claims the benefit of U.S. Provisional Patent Application No. 61/514,418, filed 2 Aug. 2011, each of which is incorporated in its entirety herein by this reference.

TECHNICAL FIELD

This invention relates generally to the field of neuroscience, and more specifically to new and useful methods for modeling neurological development, for diagnosing a neurological impairment of a patient, and for tagging an EEG signal.

BACKGROUND

The structure or topology of neural networks is a key factor in determining brain function. "Connectivity disorders," such as autism, epilepsy, and Schizophrenia, have developmental components and typically emerge at specific developmental stages of an individual. These connectivity disorders are thought to result from inappropriate development of neural network structure, on some scale, in some regions of the brain. In more specific terms, connectivity disorders may include over-dense arborization of local neurons, lack of long-range connectivity, or a combination thereof. While this is generally accepted within the scientific community, there is not a noninvasive way to measure the connectivity structure of brains.

Thus, there is a need in the field of neuroscience to create a new and useful methods for modeling neurological development, for diagnosing a neurological impairment of a patient, and for tagging an EEG signal. This invention provides such new and useful methods.

Discovery

Network structure and the time series produced by the network (in the form of electrical signals from neural spiking) are related. Recent advances in the physics of fractal networks (also known as "scale-free" or "complex" networks) demonstrate that fractal networks will produce chaotic time series or electrical signals that carry information about the network structure. This information cannot be extracted with conventional linear analysis methods (e.g., Fourier decomposition, PCA). Rather, this information is "hidden" in the nonlinear characteristics of the time series. Computing nonlinear characteristics from EEG signals contains information about the brain's network structure that can be used to discern abnormalities. If the abnormalities are distinctly associated with neurological impairments (defined by behavioral and cognitive tests), then the abnormalities may serve as biomarkers for those disorders.

BRIEF DESCRIPTION OF THE FIGURES

FIG. 1 is a flowchart representation of a method of a embodiment;

FIG. 2 is a flowchart representation of one variation of the method;

FIG. 3 is a flowchart representation of a method of a second preferred embodiment;

DESCRIPTION OF THE PREFERRED EMBODIMENTS

Figure 4:
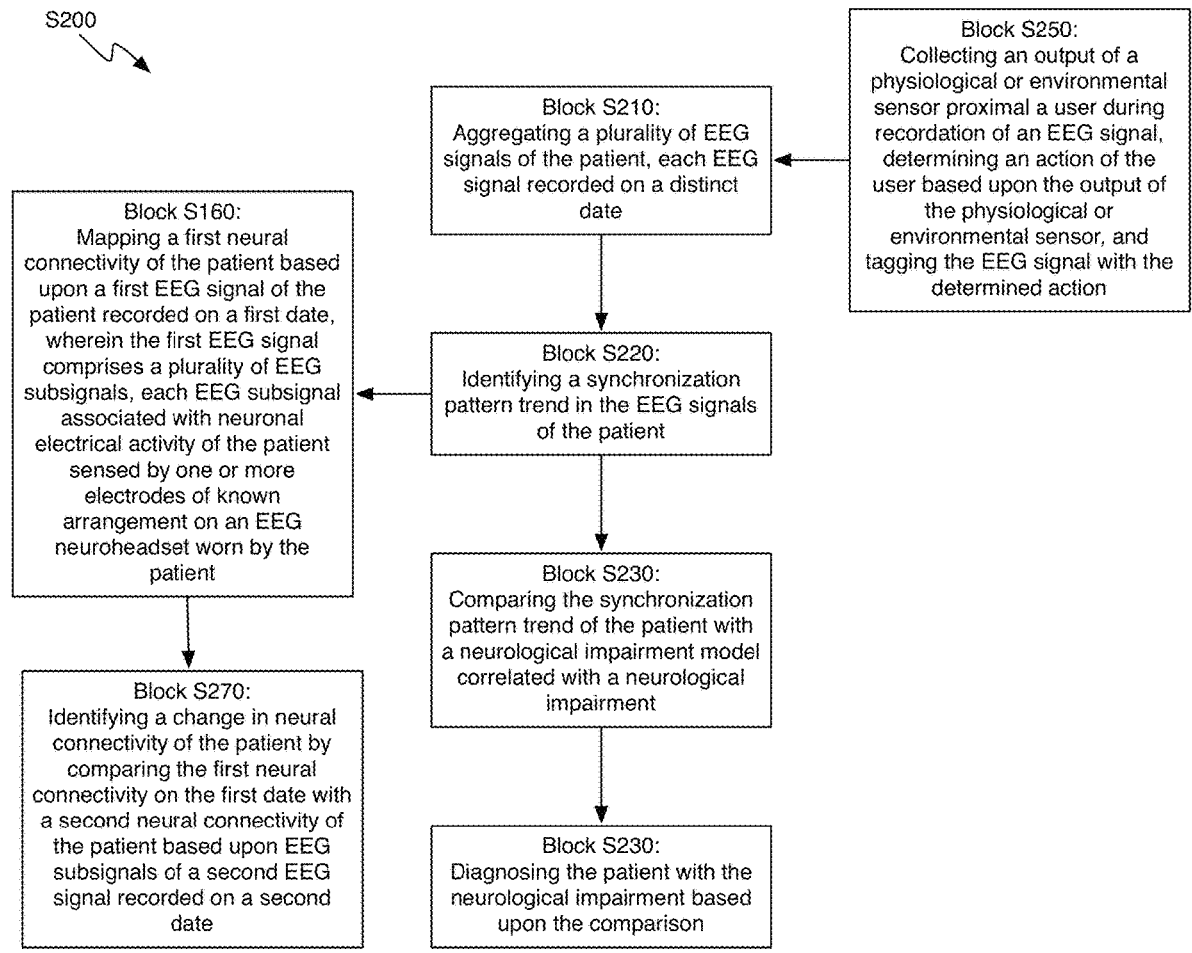
FIG. 4 is a flowchart representation of one variation of the method.

The following description of preferred embodiments of the invention is not intended to limit the invention to these embodiments, but rather to enable any person skilled in the art to make and use this invention.

The preferred embodiments of the invention include (1) a method for modeling neurological development, (2) diagnosing a neurological impairment of a patient, and (3) tagging EEG signals. Within this document, the phrase "neurological impairment" includes neurological disorders (such as Parkinson's, Alzheimer's, epilepsy, and impairments due to stroke and traumatic brain injury), developmental disorders (such as mental retardation, Autism, epilepsy, ADHD, cerebral palsy and similar motor disorders, and speech impairments), and other related developmental disorders. Furthermore, within this document, "EEG data" or "EEG signal" includes electroencephalography (EEG) data or signals but may additionally or alternatively include magnetoencephalography (MEG) or other neuronal electrical activity sensor data or signals.

1. Method for Modeling Neurological Development

As shown in FIG. 1, a method S100 for modeling neurological development includes: aggregating electroencephalography (EEG) data that include multiple EEG signals of each user in a set of users in Block S110, EEG signals of each user recorded on multiple distinct dates, the set of users including multiple users of various known neurological statuses; identifying a synchronization pattern trend within the EEG data of the set of users in Block S120; and correlating the synchronization pattern trend with neurological development within the set of users in Block S130.

The method S100 preferably functions to collect multiple EEG signals from multiple users, each user supplying at least two EEG signals recorded on two separate dates and to correlate time-stamped EEG signal features with neurological development of the users. The data may be collected from individuals participating in standardized activities or subject to similar or identical stimuli, or may be derived from EEG recordings during ordinary activities. The users are preferably individuals in a large user base, and the neurological status of each user in the user base is preferably known, previously diagnosed, or otherwise available. The method S100 preferably collects multiple EEG signals for each user, wherein EEG signals of one user are recorded on multiple different days. By extracting EEG features from a large number of EEG signals across a large (and diverse) user base and then correlating the extracted features with neurological development for at least a subset of users, the method S100 can identify current or changes in neural connectivity of one or more users, current or changes in neurological structure of the one or more users, or markers for neurological impairments of one or more users. The user base preferably includes users of various neurological statuses, including users diagnosed with a neurological impairment and users not diagnosed with the neurological impairment. By accessing user neurological statuses that include neurological conditions, the method S100 can generate a 'neurological impairment model' of one or more neurological impairments based upon a comparison of trends or features in EEG signals of users with diagnosed neurological conditions and trends or features in EEG signals of users without diagnosed neurological conditions. The neurological impairment model can then be compared with an EEG signal of a patient to enable detection and/or diagnosis of a neurological condition of the patient, such as in the method S200 described below.

Alternatively, the first preferably method S100 can generate a 'neurological connectivity model,' a 'cognitive development model,' and/or a 'neurological structure model' by comparing users of similar and/or different neurological statuses, demographics, locations, culture backgrounds, education, family history, etc. The neurological impairment model, the cognitive development model, the neurological connectivity model, and the neurological structure model are preferably time-dependent models including images of neurological development of multiple users over time. However, any one or more of the neurological impairment model, the cognitive development model, the neurological connectivity model, and the neurological structure model can be a single instance model, such as including single neurological images of multiple users. The output of the method S100 can therefore be useful in diagnosing a neurological disease of, setting a teaching curriculum for, identifying strengths and weaknesses of, tracking neurological development of, or informing improved interactions with a user, such as through the second preferred method S200.

The method S100 is preferably implemented by a computer system that collects EEG signals from EEG sensors worn by users within the user base. The computer system is preferably cloud-based (e.g., Amazon $EC_3$), but may be a mainframe computer system, a grid-computer system, or any other suitable computer system. EEG data are preferably collected by the computer system over a computer network, such as the Internet. The computer system preferably includes one or more processors configured to analyze EEG data and one or more data storage modules configured to store EEG data and a neurological impairment or other model. Furthermore, the computer system is preferably accessible by any of a user, a doctor, a patient, an employer, a teacher, a spouse, a family member, a psychiatrist, a therapist, a military agent, an insurance agency, etc. to inform future interactions with or medical diagnoses of a user or patient. EEG data, neurological development, the neurological impairment model, etc. are preferably accessible through a web browser or native application executing a digital multimedia device, such as a laptop computer, a desktop computer, a tablet, a smartphone, a personal data assistant (PDA), a personal music player, or a hospital server, though the EEG data, neurological development, the neurological impairment model, etc. can be accessed in any other way, through any other suitable device, and/or by any other entity. Furthermore the local computer or other data collection device may be configured to deliver standardized stimuli or activities to the user with a means to time-lock said stimuli or activities to the EEG data recording system for later analysis and development of the neurological impairment model.

Block S110 of the method S100 recites aggregating EEG data that comprise multiple EEG signals of each user in a set of users, EEG signals of each user recorded on multiple distinct dates, the set of users comprising a plurality of users of various known neurological statuses, with or without the participation of the user in standardized activities or stimuli. Each EEG signal is preferably recorded through a neuro-headset worn by a user in the user base. For example, each user can record an EEG signal through an Emotiv EPOC neuroheadset, a neuroheadset described in U.S. Publication No. S2007/0066914 and in U.S. Publication No. S2007/0173733 (both of which are incorporated in their entirety by reference), or any other suitable EEG sensor, electrode, or headset. Each neuroheadset preferably includes multiple electrodes (e.g., fourteen electrodes, nineteen electrodes) that, when worn, contact certain regions of the scalp of a user. Each electrode preferably senses electrical disturbances along the scalp of the user, such as a voltage change across two electrodes (e.g., across a sense electrode and a ground or reference electrode). Each EEG signal therefore preferably includes multiple subsignals, each subsignal output by at least one electrode of a neuroheadset and representing an electrical disturbance proximal an associated electrode or across two electrodes. The arrangement of each electrode is also preferably predefined or known such that each subsignal can be correlated with user neuronal activity in a region of the brain proximal the associated electrode. Furthermore, each neuroheadset is preferably sized for or adjustable to fit a user such that the neuroheadset can be repeatedly adorned and removed by the user with each electrode in the headset retained against substantially the same area of the scalp with each subsequent application.

Neuroheadsets (or other sensors, etc.) worn by the users to record EEG signals preferably define a distributed network of EEG sensors. Generally, the distributed network preferably includes a large number of neuroheadsets, each worn by at least one user in the user base and preferably defining a network node. The user base is preferably substantially large, such as including hundreds, thousands, or millions of users, and the distributed network is therefore also substantially large, such as including hundreds, thousands, or millions of nodes (e.g., neuroheadsets). Each user in the user base preferably takes multiple EEG recordings over the course of several days, weeks, or years, and each EEG recording is preferably communicated to the computer system, wherein each EEG signal is aggregated with previously-stored EEG signals of both a respective user and other users in the user base.

Additionally or alternatively, magnetic field signals from an MEG machine or images from a CAT, MRI, or any other sensor, machine, or imaging system capable of recording neurological activity of a user can be aggregated, analyzed, and correlated via the method S100. However, the EEG sensors or other devices that capture neurological states or neurological activity of the users in the user base are preferably accessible to the users in residential and/or commercial settings rather than solely in medical or clinical settings, thus enabling users to record EEG signals at various times, in various environments, while engaging in various activity, and/or while experiencing various moods or emotion states. The method S100 can therefore aggregate a colorful dataset of EEG signals corresponding to a wide variety of users of widely varying demographic, neurological condition, personality, activity, mood, emotion etc., collected either in normal activity or associated with standardized activities or stimuli which may enable greater insight into neuronal development and neurological conditions. A neurological impairment model generated through analysis of the colorful dataset may further improve accuracy and speed of neurological diagnoses when implemented in the method S200.

Each EEG signal is preferably recorded over a period of time and therefore represents a time-lapse of electrical activity across a portion of the scalp of a user. For example, an EEG signal can be twenty seconds, three minutes, or an hour long, or of any other length. EEG signals can be recorded at set times for a user, such as 10 AM PST every Monday for a year, can be recorded during specific events, such as while a user is eating dinner every weekday for two months, or can be recorded substantially haphazardly, such as whenever a user is inclined to record an EEG signal.

At least some EEG signals are preferably tagged with a neurological status of respective users. A neurological status tag includes any concentration, focused or engaging task/activity, cognitive or mental task/activity or standardized activity or stimulus. A neurological status tag preferably also includes any diagnosed neurological disorder (e.g., Parkinson's, Alzheimer's, epilepsy), developmental disorder (e.g., mental retardation, Autism, epilepsy, ADHD, cerebral palsy), or cognitive disorder (e.g., amnesia, dementia), though the neurological status tag can also include a motor disorder, speech impediment, depression, addiction, or any other current or previous disorder or diagnosed medical condition. Generally, the neurological status tags preferably enable correlation of EEG signal features with particular neurological impairment in Block S130.

Because various user activities may activate different portions of the brain and to various degrees, neuronal electrical activity may be affected to some varying degrees with an activity or state of the user during EEG recordation. Each EEG signal is therefore preferably tagged with situational information pertaining to a respective user during EEG signal collection. This situational information can be any one or more of a location of the user, an environment around the user, a user biometric, a user activity or activity detail, a mood or emotion of the user, media content viewed by the user, or any other relevant user-related information contemporaneous with recordation of an EEG signal including standardized content or stimuli delivered over the data collection network. Situational information can be generated or captured automatically or entered manually by the user. In one example implementation, a neuroheadset transmits an EEG signal to a smartphone carried by a user, and a native application executing on the smartphone tags the EEG signal with one or more outputs from a GPS sensor, an accelerometer, a gyroscope, a camera, and/or a microphone incorporated into the smartphone. In this example implementation, when the user interacts with the smartphone during EEG signal recordation, content rendered on and/or user interactions with the smartphone can also be tagged to the EEG signal. In another example implementation, outputs of a blood oximeter, a heart rate sensor, an EKG machine, a respiratory sensor, a blood pressure sensor, and/or any other biometric sensor can be transmitted to the computer system or to a digital multimedia device (e.g., a smartphone) of a user, wherein one or more such biometric outputs is tagged to a contemporaneous user EEG signal. In a further example implementation, a calendar entry, email or telephony communication, television guide, a native application executing on a smartphone or tablet, a thermostat thermometer, floor traffic sensor, or any other suitable user-related or environmental sensor or output informs a situational tag associated with an EEG signal. In another example implementation, situational information is entered manually by the user, such as with a note or survey entered or completed through a touch screen or a web-based interface once recordation of an EEG signal is complete. For example, an EEG signal of a user can be tagged with the location of the user as determined through a GPS sensor of a smartphone carried by the user, tagged with content rendered on a display of the smartphone during EEG recordation, tagged with a time and date of the EEG signal as maintained by the smartphone, and tagged with a mood and emotion of the user entered through a touch screen on the smartphone before, during, and/or after the smartphone records an EEG signal through a wired or wireless connection to a neuroheadset worn by the user. The EEG signal can additionally or alternatively be tagged with a cognitive or mental user exercise or activity (e.g., a brain exercises or brain training task), a task that requires user focus or engagement (e.g., learning a new language, playing a musical instrument), a physical exercise or activity that is new to the user (e.g., learning to throw a baseball), or any other activity, detail, or information related to the EEG signal. In another implementation, the user can be presented with a series of standardized stimuli such as questionnaires, still and video images and/or audio sequences, games or interactive activities chosen to elicit certain reactions, and the EEG data stream is time-stamped with markers indicating the exact moment of delivery of each successive stimulus. This data can be analyzed for each user or aggregated over large groups of users of known or proposed neurological statuses.

As shown in FIG. 2, a variation of the method S100 can include Block S150, which recites determining an action of the user based upon the output of a physiological or environmental sensor. The physiological or environmental sensor is preferably proximal a user during recordation of an EEG signal and is preferably configured to sense an environmental condition or a condition of a user. For example, the physiological or environmental sensor can be an accelerometer incorporated into a neural headset, a GPS sensor in a cellular phone carried by the user, a thermometer or thermostat in a room occupied by the user, or any or any other aforementioned or suitable sensor. By analyzing a sensor output, Block S150 preferably estimates an action performed by a user while an EEG signal of the user is recorded, and this estimated action is preferably tagged to its contemporaneous user EEG signal. For example a pulse oximeter outputting a high user respiratory rate and an accelerometer outputting sinusoidal vertical oscillations in the range of 1.2-1.6 Hz can suggest that the user is jogging, and a jogging tag is added to a contemporaneous user EEG signal in Block S150. Similarly, a pulse oximeter outputting a low user respiratory rate and an accelerometer indicating little or no user movement can suggest that the user is sleeping or resting, and a sleeping or resting tag is added to a contemporaneous user EEG signal in Block S150. In another example, a GPS sensor output that identifies the user at a first coordinate can indicate the user is at work while a GPS sensor output that identifies the user at a second coordinate can indicate the user is at home, and an activity commonly associated with those locations (e.g., working, sleeping) is added to a contemporaneous user EEG signal in Block S150. Block S150 can additionally or alternatively implement any of machine learning, machine vision, object recognition, audio transcription or voice detection, or any other suitable technique to extrapolate relevant user or environmental information from the sensor to determine an action of the user during EEG recordation. However, sensor data can be analyzed in any other way to extract relevant user situational information.

Alternatively, as shown in FIG. 2, another variation of the method S100 includes Block S140, which recites directing a user to perform a specified action during recordation of an EEG signal and tagging the EEG signal with the specified action. Generally, Block S140 preferably handles transmission of an action directive for the user, such as a directive to eat, rest, exercise, read a book, watch a television show, or work. The directive is preferably transmitted to the user in the form of a notification accessible through a native application executing on a digital multimedia device carried by the user. Alternatively, the directive can be communicated to the user in the form of an email, SMS text message, calendar update or alert, voicemail, or any other suitable form of communication. The directive can additionally or alternatively include a preferred time to perform an action and a reminder to wear a neuroheadset while performing the action. Details of the directive presented to the user preferably further inform a tag that is associated with an EEG signal recorded while the user performs or is expected to perform an action noted in the directive. For example, Block S140 can communicate to a user a directive to make an EEG recording while walking his dog between 6:30 and 7:00 the following morning. In anticipation of the user performing the desired action, Block S140 tags an EEG recording completed and uploaded to the computer system at 7:04 on the following morning with the 'walking dog' action tag as noted in the directive. Generally, a directed action is preferably tagged to its anticipated contemporaneous user EEG signal in Block S140. Block S140 can additionally or alternatively handle distribution of a visual, audible, or haptic stimulus to a user prior to or during EEG signal recordation. Details of a stimulus are preferably tagged to a contemporaneous user EEG signal. However, Block S140 can function in any other way.

Additionally or alternatively, a user can manually enter an action or environmental tag to be paired with an EEG signal. In this implementation, once a user completes an EEG recording, he can access a web browser or native application executing on a smartphone or computer to enter details of the recording, such as where and when the signal was recorded as well as what the user was doing, an environment proximal the user, and/or a user mood, emotion, or feeling during EEG recordation. In one example implementation, the user complete an online survey once a new EEG signal is uploaded to the computer system, and the computer system tags the EEG signal with relevant data based upon the survey. However, a user can provide any other suitable detail in any other way, and the method S100 can extract any other suitable information from a user input to generate a tag for a user EEG signal.

Each EEG signal is also preferably tagged with personal or demographic information of a respective user. For example, the age, gender, handedness, occupation, hobby, interest, education level, spoken language(s), familial history, and/or cultural background can be noted with an EEG signal of each user. Generally, situational and/or personal user information preferably identifies inputs, environmental influences, internal factors (e.g., mood, emotion), and/or human characteristics that may affect user neuronal activity. However, an EEG signal can be tagged with any other suitable neurological impairment, situational information, timing of standardized activities or stimuli, or personal information of a respective user to improve correlation of EEG signals with a neurological impairment in Block S130.

EEG signals captured by neuroheadsets across the distributed network and any relevant neurological, situational, and/or personal tags are preferably transmitted to the computer system via wired or wireless connections with Internet-accessible digital multimedia devices. Furthermore, EEG signals and any relevant tags are preferably encrypted and/or anonymized such that data transmission between a local user device and a computer system conforms to all relevant user and patient privacy regulations (e.g., HIPAA). EEG signals and/or tags are preferably encrypted according to a cryptographic protocol such as Diffie-Hellman key exchange, Wireless Transport Layer Security (WTLS), or any other suitable type of protocol. EEG signals can also be encrypted according to encryption standards such as the Data Encryption Standard (DES), Triple Data Encryption Standard (3-DES), or Advanced Encryption Standard (AES).

Block S120 of the method S100 recites extracting a synchronization pattern trend from the EEG data. Generally, Block S120 preferably analyzes EEG signals from users to identify interacting (nonlinear) dynamical systems that describe neuronal activity and therefore brain function and neural connectivity of the users. Block S120 therefore preferably functions to reveal information pertaining to a human neural network structure that is otherwise "hidden" in characteristics of EEG time-series signals.

Block S120 preferably includes comparing synchronization patterns emerging from multiple EEG signals of a particular user and recorded on multiple distinct dates to identify a synchronization pattern trend of the user. Generally, Block S120 preferably compares two EEG signals recorded on different dates but while the user was engaged in substantially the same or similar activities. Block S120 can thus isolate synchronization patterns that are common to a particular task or activity for the user from synchronization patterns that are erroneous, haphazard, or only loosely correlated with the user task or activity. By identifying synchronization patterns common to a particular user task or activity, Block S120 can filter out synchronization patterns that may be significantly affected by factors substantially unrelated to the user activity or task, such as user stress level, user mood, user energy level, or a past or upcoming task. This can significantly increase the accuracy and/or precision of a correlation between an extrapolated user synchronization pattern trend and one or more neurological conditions, as in Block S130.

Block S120 can similarly compare synchronization patterns of EEG signals of a user recorded at various times or during various tasks or activities to identify user neuronal activity not tied to a specific action, activity, task, or brain function. Certain synchronization patterns or EEG signal features correlated with this neuronal activity can then be filtered out of the EEG data as noise, parasympathetic brain function, etc. Alternatively, this neuronal activity can be used to map basic neural connectivity in the brain of the user. For example, substantially constant neuronal activity can be compared to changes in neuronal activity over time to identify which portion of the brain of the user are and are not developing.

In one example implementation of the method S100, Block S120 implements fast Fourier transform (FFT) computation to determine synchrony between frequency bands of an EEG signal. In this example implementation, Block S120 preferably includes filtering an EEG signal of a user, comparing two filtered bands of the EEG signal through spectral analysis, and extracting stable phase-difference (e.g., decoupling) or phase-locking (e.g., coupling) episodes between the two signal bands via statistical identification of phase-locking synchrony. By similarly analyzing EEG signals from other users, the preferred method can aggregate a set of phase-difference or phase-locking episodes, wherein features of the episodes (e.g., frequency, magnitude, duration, neuronal location) can be correlated with a neurological impairment in Block S130, such as based upon users with a similar neurological condition who exhibit similar phase-difference episodes distinct from phase-difference episodes of users without the neurological condition. Additionally or alternatively, Block S120 can include filtering an EEG signal of a first user and an EEG signal of a second user, comparing filtered bands of the EEG signals through spectral analysis, and extracting stable phase-difference episodes between the two EEG signals via statistical identification of phase-locking synchrony. In this example implementation, Block S130 can correlate features of the EEG signals of the users with a neurological impairment by isolating phase-difference episodes of users with similar neurological conditions from phase-difference episodes of users with differing neurological conditions.

In another example implementation of the method S100, Block S120 implements empirical model decomposition. In this example implementation, Block 120 preferably extracts intrinsic modes from an EEG signal and applies a Hilbert transform to each mode to calculate phase synchrony between frequency bands of the EEG signal.

Alternatively, Block S120 can calculate synchrony entropy (e.g., a spatio-temporal variability of synchrony between unstable dynamical systems), a Lyapunov exponent, multiscale properties of a time-series, a phase-space reconstruction of a time-series, a multichannel synchronization parameter, or any other suitable parameter or EEG signal feature to assess linear or nonlinear coupling between EEG frequency bands and/or between EEG signals, such as through multiscale entropy (MSE) analysis. However, Block S120 can implement any other technique or analysis to extract relevant features or metrics from one or more EEG signals.

Block S120 preferably identifies one synchronization pattern trend in one channel (i.e. one subsignal of an EEG signal) pertaining to one or two electrodes of a neuroheadset worn by a respective user. Block S120 preferably further identifies synchronization pattern trends in additional channels pertaining to other electrodes of the neuroheadset, thereby outputting multichannel cross-band synchronization patterns.

Figure 7:
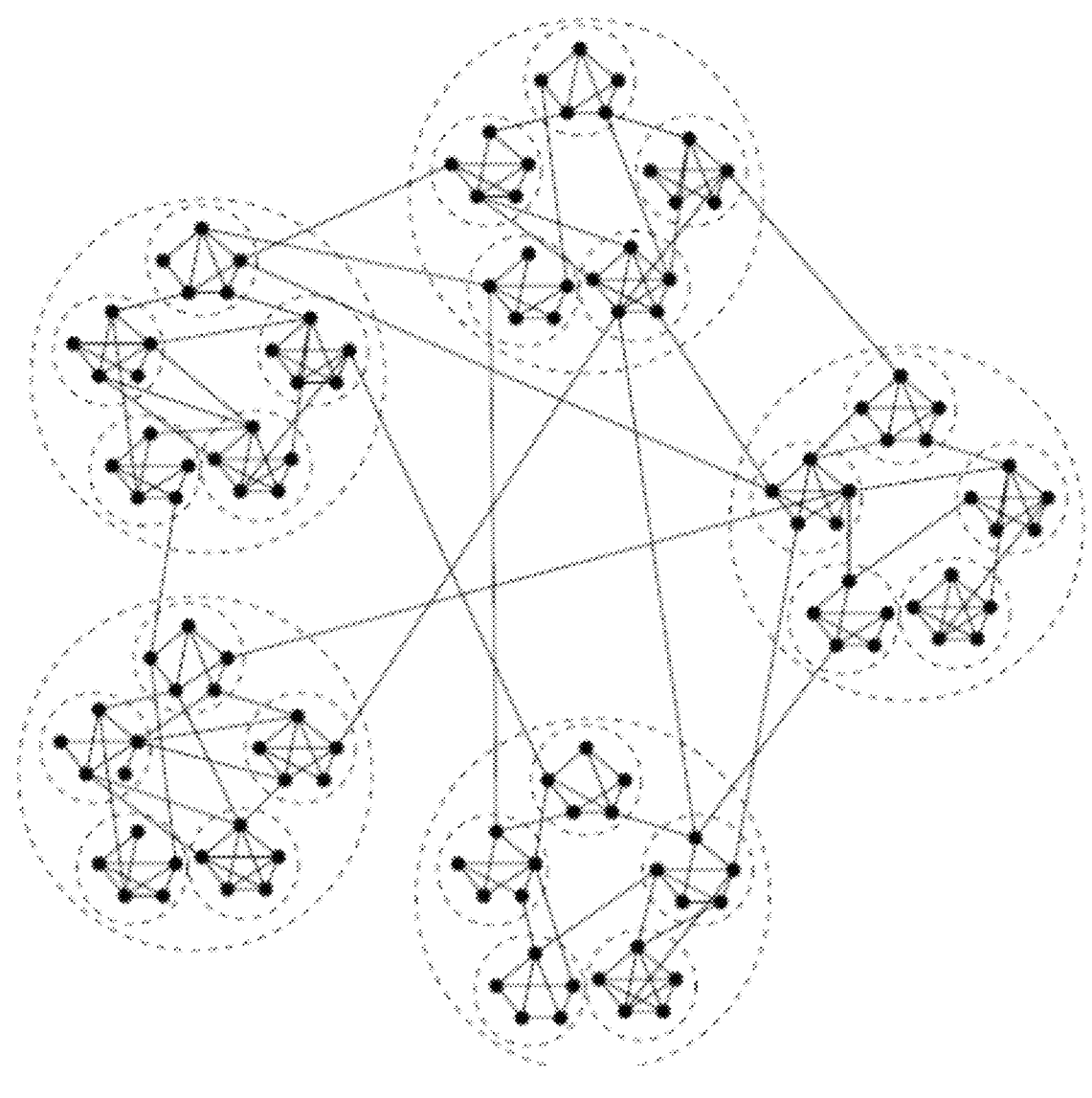
FIG. 7 is a graphical representation of a neural network.

Through any one or more of the aforementioned implementations or methods, Block S120 preferably extracts a synchronization pattern trend of a user from the EEG signals of the users. Block S120 can further compare EEG signals of multiple users to extract a synchronization pattern trend within a group of users. Generally, Block S120 preferably identifies, from multiple EEG signals recorded on two or more distinct dates, a synchronization pattern trend that is at least one of a feature, a time-series, an entropy curve, a phase-difference episode, a phase-locking episode, a dynamical neuronal subsystem, a neural network structure or topology, or an emergent hierarchical neuronal cluster (as shown in FIG. 7). The synchronization pattern trend preferably incorporates a time element correlated with neural development or changes in neural connectivity for a user over time. Generally, the synchronization pattern trend of a user can be compared with synchronization pattern trends of other users in Block S130 to correlate a neurological condition with a synchronization pattern, an EEG signal, and/or neuronal activity.

Block S130 of the method S100 recites correlating the synchronization pattern trend with neurological development within the set of users. Generally, Block S130 preferably remotely correlates the synchronization pattern trend with neurological development to generate a neurological impairment model that can be accessed in the method S200 to diagnose a neurological condition of a patient. Alternatively, Block S130 can generate a 'neurological connectivity model' or a 'neurological structure model' by comparing users of similar and different neurological development or statuses.

As described above, Block S130 preferably compares a synchronization pattern trend of EEG signals of a first user with a synchronization pattern trend of EEG signals of a second user and thereby isolates similarities and/or differences between the synchronization pattern trends. Neurological condition tags associated with each EEG signal (or respective user) preferably enable identification of synchronization pattern similarities between users with similar neurological conditions, as well as identification of synchronization pattern differences of users with different neurological conditions. By grouping similarities and differences in synchronization pattern trends of users of varying neurological condition within the user base, a model of synchronization pattern trends and correlated neurological conditions can be extrapolated from the EEG dataset. Block S130 preferably correlates the synchronization pattern of at least one EEG channel with a neurological condition, though Block S130 can augment this a correlation of additional synchronization patterns of additional EEG channels with the same or other neurological condition. For example, Block S130 can implement multichannel cross-band synchronization analysis. Block S130 preferably further bolsters or 'tunes' the neurological impairment model with additional EEG signals (and subsignals) provided over time by users in the user base.

Block S130 preferably filters comparisons between EEG signals of different users based upon demographic and/or situational information associated with the users. In one example implementation, Block S130 compares EEG signals of two users, each recorded while the users were performing similar actions, such as reading, walking, sleeping, or working. In this example implementation, Block S130 also selectively excludes comparison of EEG signals recorded while respective users were engaged in dissimilar activities, such as reading and exercising, eating and sleeping, or working and talking with a friend. In another example implementation, Block S130 compares EEG signals of two users of a similar demographic, such as same age group, same gender, or similar occupation, and Block S130 further selectively excludes comparison of EEG signals of two users of a dissimilar demographic. However, Block S130 can compare EEG signals according to any other similar or dissimilar factor, demographic, or environmental condition. By grouping EEG signals (or their respective extracted synchronization patterns) according to demographic, environmental, and/or personal information, Block S130 can minimize errors in derived corollaries between EEG synchronization patterns and neurological conditions.

Block S130 preferably extracts baseline EEG data from each user such that other users actions, mental states, etc. can be compared with the baseline EEG data to enable correlation of neural activity with particular user actions, mental states, standardized stimuli, etc. Block S130 preferably tags EEG signals recorded while the user is sitting with eyes open and/or eyes closed while breathing softly but regularly as a baseless EEG signals, as these signals may capture a minimal amount of brain activity. For example, Block S130 can subtract a baseline user EEG signal from an EEG signal recoded while the user was reading a novel to generate a composite EEG signal increased user brain activity associated with reading. Block S130 can thus compare EEG baseline signals with EEG signals associated with other particular user actions or states to isolate user neuronal activity unique to a subset of user actions or mental states.

Figure 6:
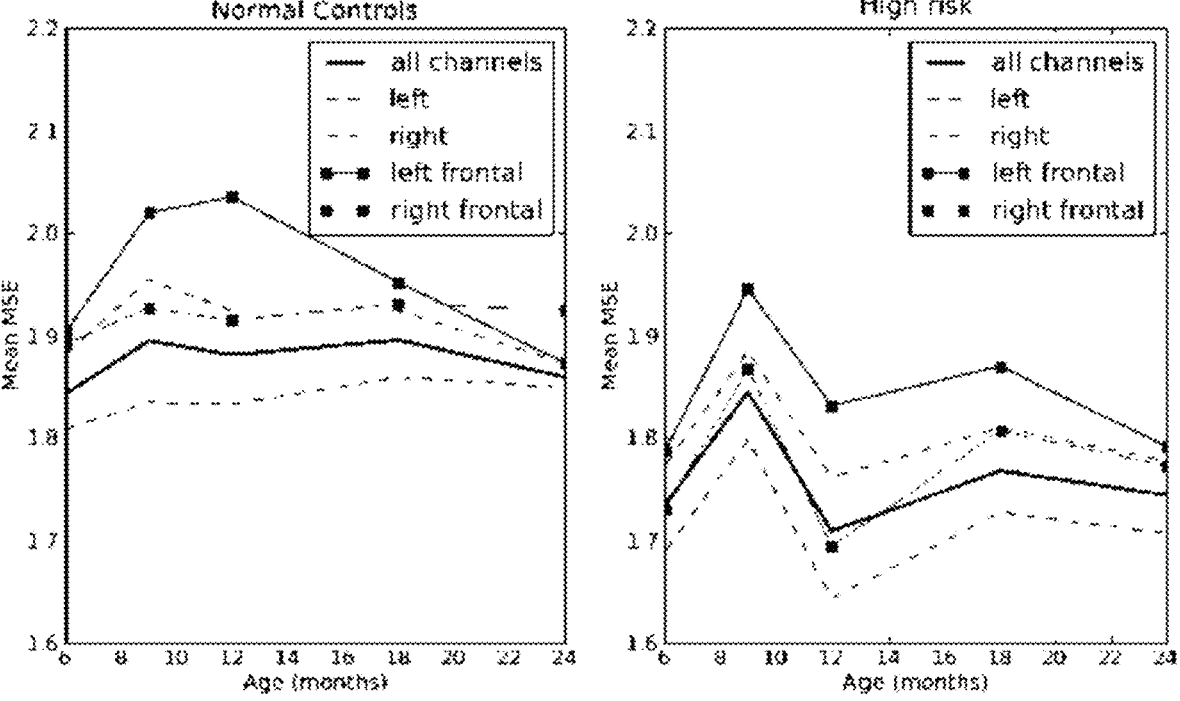
FIGS. 6A and 6B are graphical representations of neurological impairment models of users that are of low-risk and with diagnosed neurological impairments, respectively.

Block S130 preferably also filters comparisons between EEG signals of different users based upon neurological conditions of the users. In one example implementation, Block S130 constructs a baseline neurological impairment model by comparing synchronization patterns of a first set of users with no known neurological impairments with (1) synchronization patterns of a second set of users with a first diagnosed neurological impairment but no other significant neurological impairment and (2) synchronization patterns of a third set of users with a second diagnosed neurological impairment but no other significant neurological impairment. Block S130 can further repeat this comparison for additional sets of users with other neurological impairments. This baseline, single-dimension (i.e. single neurological impairment) correlation between brain activity and neurological impairment can thus define a foundation for identifying EEG signal synchronization pattern characteristics indicative of single neurological impairments in future users or patients. In this example implementation, once the baseline is constructed, synchronization patterns of users with more complex neurological impairments, such as two or more diagnosed impairments, can be compared with synchronization patterns of users with fewer or no diagnosed neurological impairments to construct a multi-dimensional model of neurological impairments and correlated synchronization patterns. Multiple neurological impairments may affect neuronal activity and therefore synchronization patterns in non-linear or non-combinatorial ways, and Block S130 can therefore identify (unique) synchronization patterns that correlate with neural interactions between multiple neurological conditions. Block S130 can therefore generate a neurological impairment model including catalogued synchronization pattern 'fingerprints' that can be compared with synchronization patterns and/or EEG signals of future users or patients to identity and diagnose one or more neurological impairments. The neurological impairment model preferably accounts for user demographic, activity, location, mood, emotion etc., environmental conditions, time, repetition, etc. by grouping and comparing synchronization pattern trends according to one or more of these details. For example, Block S130 can generate a neurological impairment model including a control model graphically represented as mean entropy curves of low-risk users (shown in FIG. 6A) and a high-risk model graphically represented as mean entropy curves of users with a particular diagnosed neurological impairment (shown in FIG. 6B).

Block S130 can further implement machine learning to tag and cluster synchronization patterns of certain EEG signals. Block S130 can also implement machine learning when augmenting an existing neurological impairment model with a recent remote patient diagnosis, such as generated through the method S200.

In an example implementation of the method S100, Block S120 includes calculating synchronization patterns that include synchronous band oscillations within an EEG signal, and Block S130 includes extracting neurological function of a user from these synchronous band oscillations. For example, synchronous gamma oscillations can be correlated with temporary representation of complex objects in user working memory and/or a mechanism by which to tie brain regions involved in associative learning into Hebbian cell assemblies. Local synchronization in the theta band can be correlated with information encoding and retrieval in episodic memory. Theta band coupling between frontal and post rolandic cortical regions can be further correlated with a retention interval of visual working memory tasks and/or an N-back working memory task. Stronger theta band coherence can be correlated with a higher intelligence. Local desynchronization in the lower alpha band can be correlated with attentional processes, and upper alpha band desynchronization can be correlated with semantic memory. Block S130 can thus identify neuronal connectivity pathways across portions of the brain of a user, which can be forward or reverse linked to a neurological impairment or condition. Therefore cross-band nonlinear (or linear) synchronization pattern trends across particular channels can be correlated with particular neural functions, and Block S130 can aggregate these patterns, channels, and neural functions to generate and grow the neurological impairment model.

As shown in FIG. 2, one variation of the method S100 further includes Block S160, which recites mapping a first neural connectivity of a user based upon a first EEG signal of the user recorded on a first date. As described above, an EEG signal preferably includes multiple subsignals output by multiple (e.g., fourteen, nineteen) electrodes incorporated into a neuroheadset. By analyzing and comparing the EEG subsignals correlating with brain activity, Block S160 can map clusters of connected neurons and neuronal pathways in a user's brain, such as graphically represented in FIG. 7. Block S160 can further analyze EEG signals recorded at other distinct times or during other user activities to generate and/or improve a neural network map of connections throughout the user's brain. For example Block S160 can aggregate user EEG signals tagged with various user activities, such as sleeping, eating, working, exercising, reading, and conversing, to identify neural connections as each portion of the brain is exercised.

In this variation of the method S100, identifying the synchronization pattern trend in Block S120 can further include identifying changes in neural connectivity of the user by comparing a first neural connectivity associated with a first date with a second neural connectivity of the user based upon EEG subsignals of a second EEG signal recorded on a second (later) date. Known or diagnosed brain development conditions of the user can then be correlated with identified changes in neural connectivity over time. For example, for a user diagnosed with autism, user neural connectivity maps may depict growing clusters of local connectivity but without longer-range connections between clusters, and this neural development (i.e. changes in neural connectivity) can be correlated with a high risk for autism.

In an example implementation, the method S100 includes: collecting information over a distributed network based upon EEG signals of users with a neurological impairment; collecting information over a distributed network based upon EEG signals from users without a diagnosed neurological impairment; computing nonlinear synchronization patterns from the information; and correlating the nonlinear synchronization patterns with neurological conditions based upon users with a (diagnosed) neurological impairment and on users without a (diagnosed) neurological impairment. In this example implementation, collection of EEG signals is split between users with and without a neurological impairment. Generally, in this example implementation, the method S100 can specifically target users with and without a known neurological impairment. Alternatively, in this example implementation, the method S100 can randomly target users and subsequently inquire about a user's mental status or neurological condition.

In another example implementation, the method S100 includes: receiving information over a distributed network based upon a series of EEG signals from users with a neurological impairment; receiving information over a distributed network based upon a series of EEG signals from users without a neurological impairment; computing nonlinear synchronization patterns from the information; and correlating the nonlinear synchronization patterns based upon the users with a neurological impairment and on the members without a neurological impairment. Compared with the first specific example, the step of receiving information now includes receiving information based upon a series of EEG signals. The series of EEG signals preferably includes a series of EEG signals recorded over a substantially long time period, such as on a daily basis for several months or on a weekly basis for several years. The extended series of EEG signals preferably facilitates correlation of user development of a neurological impairment. For a particular user, the series of EEG signals is preferably collected by the same device (or at least the same type of device with the same settings) and under similar situations (or at least under a categorized situations based upon situation information, as described above).

In a further example implementation, the method S100 includes: receiving information over a distributed network based upon EEG signals recorded during a time period associated with a user epileptic seizure; receiving information over a distributed network based upon EEG signals during a time period not associated with a user epileptic seizure; computing nonlinear synchronization patterns from the information; and correlating the nonlinear synchronization patterns based upon the time periods with an epileptic seizure and on the time periods without an epileptic seizure. This information can subsequently be aggregated to generate the neurological impairment model that includes an epilepsy model. However, the method S100 can be implemented or applied in any other way.

2. Facilitating the Diagnosis of a Neurological Impairment of a Patient

As shown in FIG. 3, a method S200 for facilitating the diagnosis of a neurological impairment of a patient includes: aggregating multiple electroencephalography (EEG) signals of the patient in Block S210, each EEG signal recorded on a distinct date; identifying a synchronization pattern trend in the EEG signals of the patient in Block S220; comparing the synchronization pattern trend of the patient with a neurological impairment model comprising a correlated neurological impairment in Block S230; and diagnosing the patient with the neurological impairment based upon the comparison in Block S240.

The method S200 preferably functions to diagnose the patient with the neurological impairment based upon a comparison of trends in EEG signals or features thereof with a neurological impairment model, such as the neurological impairment model generated by the method S100. The neurological impairment is preferably autism, epilepsy, Schizophrenia, or Alzheimer's disease, but may alternatively be any other neurological disorder, developmental disorder, cognitive disorder, etc.

As with the method S100, the method S200 preferably executes on a computer system that collects multiple EEG signals of a patient, extracts relevant features or information from the EEG signals (e.g., a synchronization pattern trend), and compares the extracted feature with a neurological impairment model to facilitate the diagnosis a neurological condition of the patient. Furthermore, the computer system that implements the method S100 can be the same computer system that implements the method S200. Alternatively, a first computer system can implement the method S100 while a separate second computer system implements the method S200, wherein the second computer system accesses the neurological impairment model of the method S100 from the first computer system. For example, the first computer system can be a remote server associated with a hospital network, and the second computer system can be a local server specific to a local hospital, wherein a physician at the local hospital initiates a patient diagnosis via the method S200 via the local server that accesses the remote server. Alternatively, the method S200 can execute on a digital multimedia device local to the patient. For example, the patient can couple a neuroheadset to his smartphone and record an EEG signal on the smartphone through the neuroheadset, wherein the smartphone accesses the neurological impairment model (e.g., downloads the model from a computer system) and locally diagnoses the patient by comparing synchronization patterns of the patient with the neurological impairment model. However, the method S200 can function in any other way and execute on any other system, server, or device.

As with the method S100, the method S200 preferably manipulates EEG signals recorded through an EEG neurological headset worn by the patient, such as in a residential or commercial setting rather that solely a medical or clinical setting. Each EEG signal also preferably includes multiple EEG subsignals output by multiple electrodes of a neuroheadset. However, an MEG signal or any other suitable neurological image can be manipulated by the method S200.

As with the method S100, each EEG signal of the method S200 is preferably tagged with personal, demographic, environmental, and/or neurological information pertaining to the patient and/or the environment proximal the patient while the EEG signal is recorded. As described above, any of this personal or situational information can be collected through a physiological or environmental sensor proximal the patient during EEG signal recordation, such as an accelerometer incorporated into a neuroheadset worn by the patient or a GPS sensor incorporated into a cellular phone carried by the patient.

Block S210 of the method S200 recites aggregating multiple EEG signals of the patient over multiple dates. Block S210 preferably collects EEG signals of the patient in a manner similar to Block S110 of the method S100.

Block S220 of the method S200 recites identifying a synchronization pattern trend in the EEG signals of the patient. Block S220 preferably identifies the synchronization pattern trend in the EEG signals of the patient in a manner similar to Block S120 of the method S100. Generally, Block S220 can extract the synchronization pattern of the patient via one or more channels of patient EEG signals recorded on multiple dates. The synchronization pattern trend is preferably at least one of a feature, a time-series, an entropy curve, a phase-difference episode, a phase-locking episode, a dynamical neuronal subsystem, a neural network structure or topology, an emergent hierarchical neuronal cluster (as represented in FIG. 7), or a multichannel cross-band nonlinear synchronization pattern. This synchronization pattern trend of the patient is then preferably compared with the neurological impairment model of the method S100 to diagnose a neurological condition of the patient in Blocks S230 and S240, respectively.

Block S230 of the method S200 recites comparing the synchronization pattern trend of the patient with a neurological impairment model correlated with a neurological impairment. Block S230 preferably compares the synchronization pattern trend in the EEG signals of the patient with the neurological impairment model in a manner similar to the methods and techniques implemented in Block S120 of the method S100 to correlate the synchronization pattern trend of the user with a neurological impairment.

Similar to the method and techniques described above, Block S230 preferably filters the neurological impairment model to select particular submodels for comparison with the synchronization pattern trend of the patient. Through filtering, Block S230 can pair a patient synchronization pattern trend with model synchronization pattern trends of users most similar to the patient or model synchronization pattern trends best fit to the patient. For example, Block S230 can filter the synchronization model according to patient demographic, situational information, patient activity, patient mood, patient location, or any other suitable personal, environmental, or external factor or information. Block S230 can implement thresholds, least mean squares, K-nearest neighbors, or any other parametric or non-parametric extrapolation to correlate a patient synchronization pattern trend with a neurological condition noted in the neurological impairment model. However, Block S230 can function in any other way.

In one example implementation of the method S200, Block S220 includes calculating synchronization patterns that include synchronous band oscillations within a patient EEG signal, and Block S230 includes determining neurological function of the patient based upon a comparison of these synchronous band oscillations with the neurological impairment model that also includes synchronous band oscillations.

Block S240 of the method S200 recites diagnosing the patient with the neurological impairment based upon the comparison. Generally, Block S240 preferably generates a diagnosis for the patient by assigning a neurological condition or status to the patient based upon an output of Block S230. Generally, the recommended diagnosis of a neurological condition preferably includes an assertion of the presence or lack of a neurological impairment in the patient, and Block S240 preferably presents this assertion to the patient or a parent, teach, physician, guardian, employer, etc. of the patient in the form of a recommended diagnosis. In one example implementation, Block S240 transmits the diagnosis directly to the patient in the form of a notification within a native application executing on a smartphone carried by the patient. In this example implementation, the preferred method can supplement the diagnosis with a recommendation for living with or improving a diagnosed neurological condition. In another example implementation, Block S240 uploads the diagnosis to a digital medical record of the patient (e.g., stored on a hospital server), wherein the medical record is accessible by a physician of the patient.

The patient EEG signals, synchronization pattern trends, and/or diagnosis can be fed back into the EEG dataset of Block S110 of the method S100 to grow and further inform the neurological impairment model of the method S100.

As shown in FIG. 4, a variation of the method S200 includes Block S260, which recites mapping a first neural connectivity of the patient based upon a first patient EEG signal recorded on a first date. Block S260 preferably maps the first neural connectivity of the patient in a manner similar to Block S160 of the method S100. In this variation, the first EEG signal preferably includes multiple EEG subsignals, and each EEG subsignal is preferably associated with neuronal electrical activity of the patient sensed at or across a particular location of the patient's scalp by one or more electrodes of known arrangement on a neuroheadset, as described above.

As shown in FIG. 4, a variation of the method S200 further includes Block S270, which recites identifying a change in neural connectivity of the patient by comparing the first neural connectivity on the first date with a second neural connectivity of the patient based upon EEG subsignals of a second EEG signal recorded on a second (later) date. Block S270 therefore preferably functions as described above. In this variation, Block S240 can additionally or alternatively diagnose the patient based upon the identified change in neural connectivity between the first and second dates. For example, Block S270 can identify an abnormality of neural connectivity of the patient, and Block S240 can diagnose the patient based upon a comparison of the neural connectivity abnormality of the patient with a neural connectivity model extracted from EEG data of multiple users of known neurological status, such as a neural connectivity model generated through the method S100. Alternatively, the Block S270 can track patient neural development trends based upon the identified change in patient neural connectivity. Trends in neural development can indicate progression or regression of a previously-diagnosed disorder, can suggest future therapy programs for the patient, and/or can inform future interactions with the patient (e.g., patient interactions with a teacher, parent, or coworker). However, Block S260 can function in any other way to output any other form of neural connectivity to enable any other diagnosis or inform any other interaction with the patient.

As shown in FIG. 4, a variation of the method S200 includes Block S250, which recites collecting an output of a physiological or environmental sensor proximal a user during recordation of an EEG signal, determining an action of the user based upon the output of the physiological or environmental sensor, and tagging the EEG signal with the determined action. Block S250 can additionally or alternatively determine an environmental condition proximal the patient during EEG signal recordation, a mood of the user, a physiological status of the user, or any other suitable information relevant to a recorded EEG signal. Therefore, Block S250 preferably identifies the action, environmental condition, etc. in a manner similar to Block S150 of the method S100.

In one example implementation, the second preferred method includes: receiving information over a distributed network based upon a series of EEG signals from a patient; computing nonlinear synchronization patterns from the information; comparing trends of the patterns of the patient with the trends of the patterns from a user with a neurological impairment; and remotely detecting patient development of a neurological impairment based upon the comparison. The series of patient EEG signals preferably includes multiple EEG signals recorded over a long time period, such as on a daily basis for several months or on a weekly basis for several years. The extended EEG series preferably facilitates correlation of the EEG signals with patient development of a neurological impairment. The patient EEG signals in the series are preferably collected by the same device (or at least the same type of device with the same settings) and under similar situations (or at least under a categorized situation based upon the situation information, as described above). In this example implementation, the method S200 can also function to provide feedback to the patient or associated entity for the abatement or reversal of the development of the neurological impairment.

In another example implementation, the method S200 includes: receiving information over a distributed network based upon EEG signals from a patient; computing a synchronization pattern from the information; comparing the patient synchronization pattern with a synchronization pattern of a user recorded during an epileptic seizure; and remotely monitoring the presence of an epileptic seizure in the user based upon the comparison. In this example implementation, the method S200 can communicating a patient diagnosis, such as for epilepsy, to a heath care professional associated with the patient or to any other suitable person or entity. This communication method can be based upon measured or determined situation information, as described above. For example, if the patient is known to be physically located within a health care facility or the his home, the communication can be directed to the health care facility or to the patient's family. Furthermore, if the patient is known to be physically located outside of a designated area, the communication can be directed to an emergency response unit.

The method S200 can further function to remotely treat development of a diagnosed patient neurological impairment. For example, the method S200 can communicate a video output (such as via a display or a projection), an audio output (such as via a speaker), a haptic output (such as via a vibration device), or any suitable feedback to the patient or an associated entity (e.g., doctor, souse, parent, teacher, or guardian) for aid in abatement or reversal of the neurological impairment. In another example, the method S200 reacts to the occurrence of an epileptic seizure in the patient, such as by communicating a video output, an audio output, a haptic output, or any other suitable feedback for minimizing patient risk during or following the epileptic seizure. The method S200 can additionally or alternatively initiate emergency contact or an emergency response based upon patient development of a neurological impairment. The method S200 can also manipulate heavy machinery control interfaces, such as a vehicle braking system and a vehicle steering system, to override patient inputs during a neurological episode, such as an epileptic seizure or stroke. However, the method S200 can function in any other way to fulfill any other desired function.

3. Tagging EEG Signals

Figure 5:
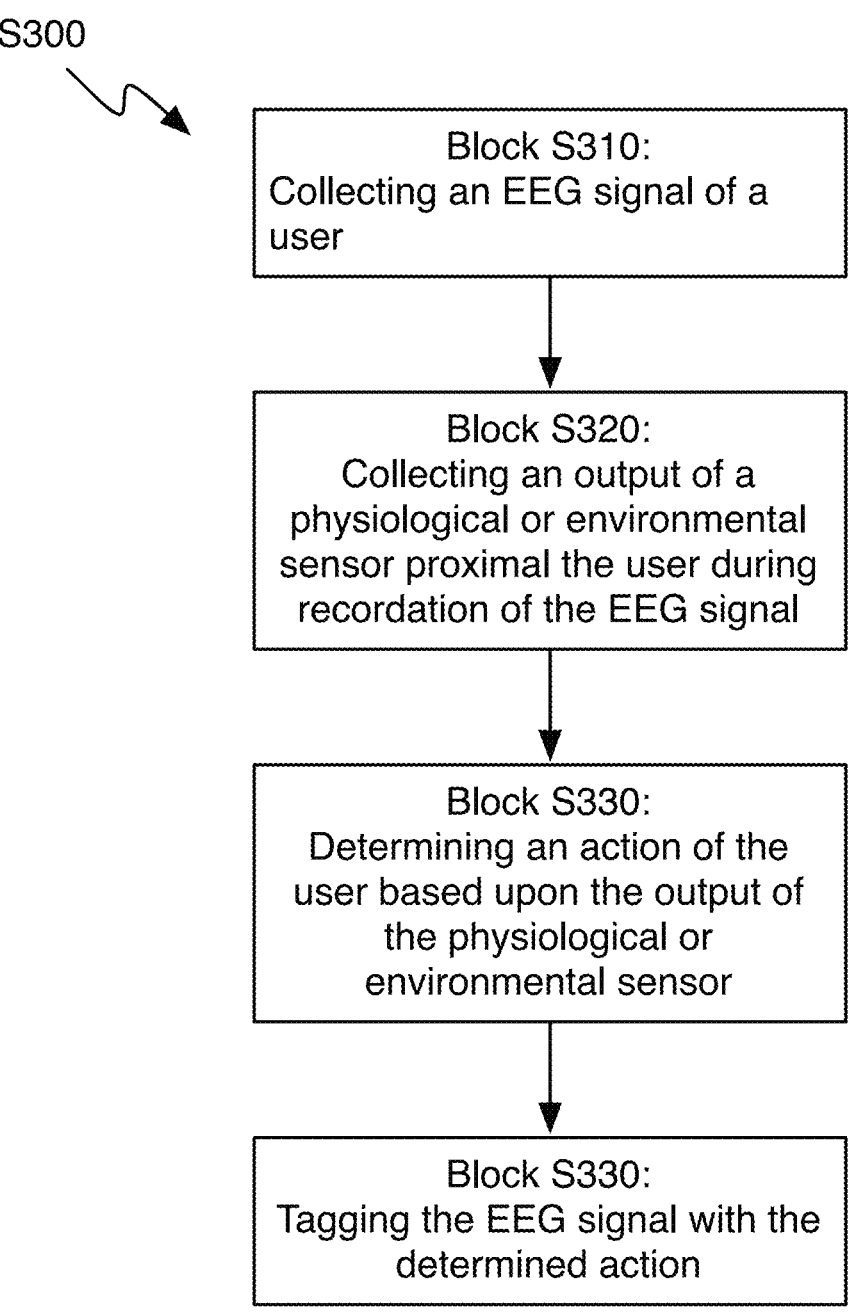
FIG. 5 is a flowchart representation of a method of a third preferred embodiment.

As shown in FIG. 5, a method S300 for tagging EEG signals includes collecting an EEG signal of a user in Block S310; collecting an output of a physiological or environmental sensor proximal the user during recordation of the EEG signal in Block S320; determining an action of the user based upon the output of the physiological or environmental sensor in Block S330; and tagging the EEG signal with the determined action in Block S340.

The method S300 functions to automatically identify an action of a user during recordation of an EEG signal by analyzing an output of a physiological or environmental sensor mounted on, carried by, or arranged proximal a user during recordation of the EEG signal. In one example, the physiological or environmental sensor is an accelerometer, a gyroscope, a camera, or a microphone incorporated into a neuroheadset or a smartphone carried by the user. In another example, the physiological or environmental sensor is a blood oximeter, a heart rate sensor, an EKG machine, a respiratory sensor, a blood pressure sensor, or any other standalone biometric sensor or biometric sensor incorporated into a neuroheadset or digital multimedia device carried by the user. However, the physiological or environmental sensor can be any other suitable sensor generating any other suitable output. The method S300 therefore preferably functions to automatically tag an EEG signal with highly-relevant user or environmental information that may significantly affect neurological activity and therefore an EEG signal of the user recordation. The method S300 therefore preferably requires little or no direct user input to generate action or environmental condition tags that can inform grouping or filtering of user EEG signals with EEG signals of other users and/or with a neurological impairment model. The method S300 may therefore significantly improve the accuracy of a neurological impairment model generated in the method S100 or diagnosis of a neurological condition of a patient in the method S200.

The method S300 is preferably implemented by the computer system that also implements the method S100 and/or the method S200. For example, a sensor output contemporaneous with an EEG signal can be communicated to the computer system along with the EEG signal, wherein the computer system analyzes the sensor output, determines a user action or status, and tags the EEG signal with the determined user action or status. The computer system can additionally or alternatively tag the EEG signal with a determined environmental or situational information, as described above, including the case where the user's activities and/or specific standardized stimuli can be directed or presented by the said computer system Alternatively, the neuroheadset can communicate EEG signals to a digital multimedia device, such as a smartphone or tablet, and a native application executing on the digital multimedia device can access a sensor signal, extract a user action or environmental condition from the sensor signal, and tag a contemporaneous EEG signal with the determined user action or environmental condition prior to communicating the EEG signal to the computer system. Therefore, the method S300 can be implemented locally, such as on a digital multimedia device carried by the user, or remotely, such as on a computer system.

Block S310 of the method S300 recites collecting an EEG signal of a user in Block S310. Block S310 preferably collects one or more user EEG signals in a manner similar to Block S110 of the method S100 and/or Block S210 of the method S200.

Block S320 of the method S300 recites collecting an output of a physiological or environmental sensor proximal the user during recordation of the EEG signal. As described above, Block S320 can locally or remotely collect an output of any physiological or environmental sensor that is a standalone sensor or that is incorporated into a neuroheadset, a digital multimedia device carried by the user, or a local digital device (e.g., thermostat, floor traffic sensor).

Block S330 of the method S300 recites determining an action of the user based upon the output of the physiological or environmental sensor in Block S330. Block S330 preferably analyzes the sensor signal and correlates the sensor signal with a particular action or condition of the user, such as described in Block S150 and Block S250 above. Block S330 can further analyze signals from multiple sensors to determine the user action or condition, such as a heart rate sensor and a GPS sensor pair, an accelerometer and a microphone pair, or a thermometer, a pedometer, and a light sensor set. Block S330 preferably includes accessing action models including markers or fingerprints of known or common actions such that a sensor signal correlated with a particular action can be paired with a user EEG signal with a suitable degree of certainty. However, Block S330 can function in any other way to determine an action of the user or environmental condition.

Block S340 of the method S300 recites tagging the EEG signal with the determined action. The action and/or environmental tag can be added to the EEG signal locally or remotely, such as on a smartphone carried by the user or on a computer system. As described above, the tag preferably informs filtering and/or grouping of EEG signals across multiple users when generating or growing the neurological impairment model, such as through the method S100. Additionally or alternatively, the tag can inform filtering and/or grouping of EEG signals when diagnosing a patient, such as by comparing patient EEG signals or synchronization pattern trends with a neurological impairment model in the method S200. However, the action and/or environmental tag generated and added to an EEG signal in the method S300 can be used in any other way.

The systems and methods of the preferred embodiments can be embodied and/or implemented at least in part as a machine configured to receive a computer-readable medium storing computer-readable instructions. The instructions are preferably executed by computer-executable components preferably integrated with the application, applet, host, server, network, website, communication service, communication interface, hardware/firmware/software elements of a user computer or digital multimedia (mobile) device, or any suitable combination thereof. Other systems and methods of the preferred embodiment can be embodied and/or implemented at least in part as a machine configured to receive a computer-readable medium storing computer-readable instructions. The instructions are preferably executed by computer-executable components preferably integrated by computer-executable components preferably integrated with apparatuses and networks of the type described above. The computer-readable medium can be stored on any suitable computer readable media such as RAMs, ROMs, flash memory, EEPROMs, optical devices (CD or DVD), hard drives, floppy drives, or any suitable device. The computer-executable component is preferably a processor but any suitable dedicated hardware device can (alternatively or additionally) execute the instructions.

As a person skilled in the art will recognize from the previous detailed description and from the figures and claims, modifications and changes can be made to the preferred embodiments of the invention without departing from the scope of this invention defined in the following claims.

We claim:

1. A computer-implemented method, comprising:
for each user of a set of users:
recording a set of EEG signals from the user, wherein recording the set of EEG signals from the user comprises: at each time point of a set of time points, at a neuroheadset of the user, recording an EEG signal; and
determining a set of synchronization pattern features for each EEG signal in the set of EEG signals;
determining a synchronization pattern trend based on the set of synchronization pattern features;
for the set of users:
organizing the synchronization pattern trends into a set of groups; and
assigning a tag to each group of the set of groups, wherein each tag is associated with a user state;
determining a model for each group of the set of groups based on the tagged set of groups;
using the determined models, determining a predicted tag for a new user; and recommending an activity for the new user to perform based on the predicted tag.

2. The method of claim 1, further comprising, for the new user:
recording a set of new EEG signals from the new user, wherein recording the set of new EEG signals from the new user comprises: at each time point of a new set of time points, at a neuroheadset of the new user, recording a new EEG signal;
determining a new synchronization pattern trend based on the set of new EEG signals;
determining a set of correlations based on the new user synchronization pattern trend and the determined models; and
determining the predicted tag based on the set of correlations.

3. The method of claim 1, wherein each user state is associated with a focused task.

4. The method of claim 1, further comprising, for the new user:
recording a set of new EEG signals from the new user, wherein recording the set of new EEG signals from the new user comprises: at each time point of a new set of time points, at a neuroheadset of the new user, recording a new EEG signal;
determining a new synchronization pattern trend based on the set of new EEG signals;
adding the new synchronization pattern trend to a group of the set of groups; and
updating the model associated with the group based on the new user synchronization pattern trend.

5. The method of claim 4, wherein the model is updated using machine learning methods.

6. The method of claim 1, wherein each tag comprises a neurological status tag.

7. The method of claim 1, wherein determining the synchronization pattern trend for each user of the set of users comprises: filtering a first EEG signal of the set of EEG signals of the user in a first band to generate a first band-filtered EEG signal; filtering the first EEG signal of the set of EEG signals of the user in a second band to generate a second band-filtered EEG signal; and extracting a set of phase locking episodes between the first band-filtered EEG signal and the second band-filtered EEG signal.

8. The method of claim 1, wherein the synchronization pattern trend is nonlinear.

9. A computer-implemented method, comprising:
for each user of a set of users:
recording a set of EEG signals from the user, wherein recording the set of EEG signals from the user comprises: at each time point of a set of time points, at a neuroheadset of the user, recording an EEG signal; and
determining a synchronization pattern trend based on the set of EEG signals, wherein determining the synchronization pattern trend comprises: generating a filtered first EEG signal and a filtered second EEG signal upon filtering each of a first and a second EEG signal of the set of EEG signals of the user, respectively; analyzing the filtered first and second EEG signals via spectral analysis; and identifying stable phase difference episodes between the filtered first and second EEG signals via statistical identification of phase-locking synchrony;
for the set of users:
organizing the synchronization pattern trends into a set of groups; and assigning a tag to each group of the set of groups,
    wherein each tag is associated with a user state;
determining a model for each group of the set of groups
    based on the tagged set of groups;
using the determined models, determining a predicted tag
    for a new user; and
recommending an activity for the new user to perform
    based on the predicted tag.

\* \* \* \* \*